United States Patent
Yu et al.

(10) Patent No.: US 12,073,943 B2
(45) Date of Patent: Aug. 27, 2024

(54) MEDICAL IMAGE ANALYSIS SYSTEM AND SIMILAR CASE RETRIEVAL SYSTEM USING QUANTITATIVE PARAMETERS, AND METHODS FOR THE SAME

(71) Applicants: Coreline Soft Co., Ltd., Seoul (KR); THE ASAN FOUNDATION, Seoul (KR); UNIV. OF ULSAN FOUNDATION FOR INDUSTRY COOPERATION, Ulsan (KR)

(72) Inventors: Donghoon Yu, Gimpo-si (KR); Jaeyoun Yi, Seoul (KR); Byeong Soo Kim, Bucheon-si (KR); Joon Beom Seo, Seoul (KR); Namkug Kim, Seoul (KR); Sang Min Lee, Seoul (KR)

(73) Assignees: Coreline Soft Co., Ltd., Seoul (KR); THE ASAN FOUNDATION, Seoul (KR); UNIV. OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 184 days.

(21) Appl. No.: 17/132,086

(22) Filed: Dec. 23, 2020

(65) Prior Publication Data

US 2021/0201495 A1 Jul. 1, 2021

(30) Foreign Application Priority Data

Dec. 31, 2019 (KR) .................. 10-2019-0179252

(51) Int. Cl.
G16H 50/20 (2018.01)
A61B 5/08 (2006.01)
(Continued)

(52) U.S. Cl.
CPC .............. *G16H 50/20* (2018.01); *A61B 5/08* (2013.01); *G06F 18/22* (2023.01); *G06T 7/0012* (2013.01);
(Continued)

(58) Field of Classification Search
CPC ........ G16H 50/70; G16H 50/20; G16H 30/20; G16H 30/40; G06T 7/11;
(Continued)

(56) References Cited

U.S. PATENT DOCUMENTS 7,724,930 B2 5/2010 Zhou et al.
7,804,990 B2 9/2010 Kiraly et al.
(Continued)

FOREIGN PATENT DOCUMENTS

KR 2015-0006807 A 1/2015
KR 2016-0140194 A 12/2016
(Continued)

OTHER PUBLICATIONS

Nakano, Y., Wong, J. C., de Jong, P. A., Buzatu, L., Nagao, T., Coxson, H. O., Elliott, W. M., Hogg, J. C., & Paré, P. D. (2005). The Prediction of Small Airway Dimensions Using Computed Tomography. In American Journal of Respiratory and Critical Care Medicine (vol. 171, Issue 2, pp. 142-146).American (Year: 2005) Journal of Respiratory and Critical Care Medicine (vol. 171, Issue 2, pp. 142-146). American Thoracic Society. https://doi.org/10.1164/rccm.200407-874oc (Year: 2005).*
(Continued)

*Primary Examiner* — Aaron W Carter
*Assistant Examiner* — Courtney Joan Nelson
(74) *Attorney, Agent, or Firm* — United One Law Group LLC; Kongsik Kim; Jhongwoo Peck (57) ABSTRACT

Disclosed herein is a computing system for performing medical image analysis. A computing system for performing
(Continued)

medical image analysis according to an embodiment of the present invention includes at least one processor. The at least one processor performs image processing on a first medical image, and segments at least one anatomical region in the first medical image. The at least one processor generates a first quantitative parameter for the at least one anatomical region based on quantitative measurement conditions that can be measured in the first medical image, and stores the first quantitative parameter in a database in association with the first medical image and the at least one anatomical region.

6 Claims, 9 Drawing Sheets

(51) Int. Cl.
*G06F 18/22* (2023.01)
*G06T 7/00* (2017.01)
*G06T 7/11* (2017.01)
*G06V 10/75* (2022.01)
*G16H 30/20* (2018.01)
*G16H 30/40* (2018.01)

(52) U.S. Cl.
CPC ............... *G06T 7/11* (2017.01); *G06V 10/75* (2022.01); *G16H 30/20* (2018.01); *G16H 30/40* (2018.01); *G06T 2207/30061* (2013.01); *G06V 10/759* (2022.01)

(58) Field of Classification Search
CPC ......... G06T 2207/30004; G06T 3/4046; G06T 7/0014; G06T 2207/30096; G06T 7/00; G06T 7/0012; G06T 7/73; G06T 2207/30061; G06F 18/22; G06F 18/214; G06F 16/2465; G06F 16/53; G06N 3/08; G06N 5/025; G06V 10/40; G06V 10/761; G06V 10/75; G06V 10/759; A61B 5/08
See application file for complete search history.

(56) References Cited

U.S. PATENT DOCUMENTS

| | | | |
|---|---|---|---|
| 8,306,960 | B2 | 11/2012 | Kakimoto et al. |
| 8,311,962 | B2* | 11/2012 | Kato ................. G06V 10/25 |
| | | | 706/20 |
| 10,007,984 | B2 | 6/2018 | Lee et al. |
| 10,133,846 | B2* | 11/2018 | Takata ................. G06T 7/0012 |
| 10,248,759 | B2 | 4/2019 | Larcom et al. |
| 10,331,851 | B2 | 6/2019 | Takata et al. |
| 10,748,662 | B2 | 8/2020 | Jung |
| 2016/0350911 | A1* | 12/2016 | Igarashi ................. G06T 7/11 |
| 2017/0011187 | A1* | 1/2017 | Oosawa ................. G06T 1/00 |
| 2019/0066847 | A1* | 2/2019 | Jung ................. G06V 20/64 |
| 2019/0197688 | A1* | 6/2019 | Moriwaki ................. G06T 7/11 |
| 2019/0267130 | A1 | 8/2019 | Takata et al. |
| 2019/0295724 | A1* | 9/2019 | Kanada ................. G16H 10/00 |

FOREIGN PATENT DOCUMENTS

| | | | |
|---|---|---|---|
| KR | 101744800 B1 | 6/2017 | |
| KR | 2017-0132995 A | 12/2017 | |
| KR | 101841496 B1 | 3/2018 | |
| KR | 101884609 B1 | 8/2018 | |
| KR | 10-2057277 B1 | 12/2019 | |
| WO | WO-2018116727 A1 * | 6/2018 | ............... A61B 6/03 |

OTHER PUBLICATIONS

Perez-Rovira, A., Kuo, W., Petersen, J., Tiddens, H. A. W. M., & de Bruijne, M. (2016). Automatic airway-artery analysis on lung CT to quantify airway wall thickening and bronchiectasis. In Medical Physics (vol. 43, Issue 10, pp. 5736-5744). Wiley. https://doi.org/10.1118/1.4963214 (Year: 2016).*

Machine translation of WO-2018116727-A1 (Year: 2018).*

I. El-Naqa, Yongyi Yang, N. P. Galatsanos, R. M. Nishikawa and M. N. Wernick, "A similarity learning approach to content-based image retrieval: application to digital mammography," in IEEE Transactions on Medical Imaging, vol. 23, No. 10, pp. 1233-1244, Oct. 2004, doi: 10.1109/TMI.2004.834601. (Year: 2004).*

* cited by examiner

| Regions | Volume (cc) | LAA (≤-950, cc) | LAA (≤-950, %) |
|---|---|---|---|
| Whole Lungs | 6243.6 | 1689.6 | 27.1 |
| Rt. Lung | 3306.8 | 941.4 | 28.5 |
| Lt. Lung | 2936.8 | 748.2 | 25.5 |
| RUL | 1850.7 | 826.8 | 44.7 |
| RML | 405.1 | 55.3 | 13.7 |
| RLL | 1051.1 | 59.3 | 5.6 |
| LUL | 1764.3 | 671.6 | 38.1 |
| LLL | 1172.6 | 76.6 | 6.5 |

| Regions | Volume (cc) | ATV (<60, cc) | ATI (<60, %) |
|---|---|---|---|
| Whole Lungs | 6243.6 | 3501.0 | 56.1 |
| Rt. Lung | 3306.8 | 2050.2 | 62.0 |
| Lt. Lung | 2936.8 | 1450.7 | 49.4 |
| RUL | 1850.7 | 1458.6 | 78.8 |
| RML | 405.1 | 281.1 | 69.4 |
| RLL | 1051.1 | 310.6 | 29.6 |
| LUL | 1764.3 | 1226.1 | 69.5 |
| LLL | 1172.6 | 224.6 | 19.2 |

MEDICAL IMAGE ANALYSIS SYSTEM AND SIMILAR CASE RETRIEVAL SYSTEM USING QUANTITATIVE PARAMETERS, AND METHODS FOR THE SAME

CROSS-REFERENCE TO RELATED APPLICATION

This application claims under 35 U.S.C. § 119(a) the benefit of Korean Patent Application No. 10-2019-0179252 filed on Dec. 31, 2019, which is incorporated herein by reference in its entirety.

TECHNICAL FIELD

The present invention relates generally to a medical image analysis method and a similar case retrieval method using a medical image analysis technology, and more particularly to a technology for constructing a system for clinically significant similar case retrieval by using a medical image analysis technology using quantitative parameters.

The present invention was derived from the research conducted as part of the Fundamental SW Computing Technology Development Project sponsored by the Korean Ministry of Science and ICT and the Institute for Information and Communications Technology Promotion [Project Management Number: 2018-0-00861; and Project Name: Development of Intelligent SW Technology for Analysis of Medical Data].

BACKGROUND ART

A clinical decision support system is a system that provides doctors with assistance with decision making by providing the function of providing required base knowledge and also helping correct reasoning when doctors make diagnoses or determine treatment policies in the treatment of patients. In the examination of a patient, in addition to the subjective decision of a doctor in charge, medically established guidelines are implemented using a computer and then the doctor is informed of the results of the guidelines on the patient's condition, thereby preventing misdiagnosis and also enabling more objective medical practice.

Korean Patent No. 10-1744800 entitled "System for Providing Medical Information" introduces a technique for extracting similar cases by applying an analytic hierarchy process (AHP) based on weights and also comparing the attribute information of a patient and the already stored case information of patients, into which the weights have been incorporated, in order to extract cases similar to that of the patient.

However, even according to this related art, the already stored case information of patients includes only diagnostic information input by doctors, and the analysis of the stored data may be analysis without clinical meaning. Typically, it is vulnerable to problems such as overfit, and the reliability of the analysis is particularly low when there is an insufficient amount of data.

Recently, with the development of artificial intelligence technology represented by machine learning based on an artificial neural network, various techniques for processing big data have been developed, and attempts have been actively made to assist in clinical decision making by applying artificial intelligence to medical information. In particular, there have been developed methods of helping clinicians make decisions by applying artificial intelligence algorithms not only to medical images acquired from diagnostic apparatuses such as an X-ray machine, an ultrasonic scanner, a computed tomography (CT) scanner, a magnetic resonance imaging (MRI) scanner, a positron emission tomography (PET) scanner, etc. but also to various types of medical information including medical histories, health-related numerical data, etc.

Attempts to process big data by applying artificial intelligence to medical information include Korean Patent No. 10-1884609 entitled "System for Diagnosing Disease through Modularized Reinforcement Learning." However, even according to this preceding literature, the focus is placed only on the classification and pattern extraction of unstructured data, and it is not clear whether or not an extracted pattern is clinically significant. Accordingly, this technique is not suitable for practical application in the medical field.

U.S. Pat. No. 10,248,759 entitled "Medical Imaging Reference Retrieval and Report Generation" is a preceding document in which a user is assumed to be a clinician or radiologist in order to acquire clinically significant data when searching for similar cases. This preceding document discloses a technique for automatically searching for images including a specific feature, receiving feedback (selection), on whether or not the corresponding images are suitable for the results of the search, from a user, and then generating a report.

U.S. Pat. No. 7,724,930 entitled "Systems and Methods for Automatic Change Quantification for Medical Decision Support" provides a means for comparing a patient's previous medical image with his or her current medical image, automatically quantifying changes in a specific area, and then generating a report.

Even according to the above-described preceding documents, the following problems still exist. First, the lack of clinically significant data remains unresolved. Second, due to analysis based on limited data, an erroneous pattern is acquired because of data overfit or a clinically insignificant pattern is acquired.

SUMMARY OF THE DISCLOSURE

The present invention has been conceived to overcome the above-described problems, and an object of the present invention is to propose a technology for the retrieval of clinically significant similar cases.

An object of the present invention is to build up a database in order to support similar case retrieval, to propose effective quantitative parameters in order to construct the database, and to propose a medical image analysis technology using the quantitative parameters.

An object of the present invention is to provide a medical image analysis technology capable of effectively supporting similar case retrieval and presenting more cases and a larger amount of information when retrieving similar cases.

An object of the present invention is to provide a technology that derives and proposes quantitative parameters to calculate similarity in order to retrieve clinically significant similar cases, represents each case image using one quantitative parameter, and retrieves similar cases based on the results of evaluation of the similarity between case images.

An object of the present invention is to provide a technology that quantifies parameters effective in the retrieval of similar cases of lung disease, determines similarity using the quantitative parameters, and retrieves similar cases based on the similarity.

According to an aspect of the present invention, there is provided a medical image analysis method that is performed by a computing system, the medical image analysis method including: performing image processing on a first medical image, and segmenting at least one anatomical region in the first medical image; generating a first quantitative parameter for the at least one anatomical region based on quantitative measurement conditions that can be measured in the first medical image; and storing the first quantitative parameter in a database in association with the first medical image and the at least one anatomical region.

The segmenting may include segmenting a plurality of anatomical regions in the first medical image. In this case, the generating may include generating a plurality of region-specific quantitative parameters for the plurality of respective anatomical regions and generating a quantitative parameter vector, including the plurality of region-specific quantitative parameters generated for the plurality of respective anatomical regions, as the first quantitative parameter.

In this case, the first quantitative parameter may be obtained based on the calculation intended to perform adjustment to assign normalized or equivalent weight by normalizing each of the plurality of region-specific quantitative parameters in the quantitative parameter vector. The quantitative parameter vector may be a feature vector generated by mapping each of the plurality of region-specific quantitative parameters into a vector space.

The generating may include: extracting at least one first region for the at least one anatomical region based on the quantitative measurement conditions; and generating a first quantitative parameter associated with the at least one first region and the at least one anatomical region by quantifying at least one of the spatial ratio of the space (measured at 2D or 3D) occupied by the at least one first region within the at least one anatomical region and a spatial distribution including the size and number of the at least one first region in association with the at least one anatomical region.

The segmenting may include segmenting a plurality of anatomical regions in the first medical image. The extracting may include extracting at least one first region for each of the plurality of anatomical regions.

The generating a first quantitative parameter associated with the at least one first region and the at least one anatomical region may include: extracting at least one Low Attenuation Area (LAA) or at least one air trap region (or volume) within the at least one anatomical region as the at least one first region; and generating the spatial ratio of the space (measured at 2D or 3D) occupied by the at least one first region within the at least one anatomical region as the first quantitative parameter associated with the at least one first region and the at least one anatomical region.

The generating a first quantitative parameter associated with the at least one first region and the at least one anatomical region may include: extracting at least one Low Attenuation Area (LAA) within the at least one anatomical region as the at least one first region; and generating the first quantitative parameter associated with the at least one first region and the at least one anatomical region based on a spatial distribution including the number of at least one first region based on (according to) the size of the at least one first region within the at least one anatomical region.

The generating a first quantitative parameter for the at least one anatomical region based on quantitative measurement conditions may include: segmenting an airway region within the at least one anatomical region; calculating a lumen perimeter and a wall area using a segmented lumen and airway wall; and generating, for each of at least one airway included in the at least one anatomical region, an airway wall area, normalized on the assumption that the perimeter of the lumen is 10 mm, as the first quantitative parameter.

According to another aspect of the present invention, there is provided a similar case retrieval method that is performed by a computing system, the similar case retrieval method including: receiving a second medical image via user input; performing image processing on the second medical image, and segmenting at least one anatomical region in the second medical image; generating a second quantitative parameter for at least one anatomical region based on quantitative measurement conditions that can be measured in the second medical image; and retrieving at least one first medical image having a first quantitative parameter similar to the second quantitative parameter of the second medical image from a database based on the similarity with the second quantitative parameter.

The segmenting may include segmenting a plurality of anatomical regions in the second medical image. The generating may include generating a plurality of region-specific quantitative parameters for the plurality of respective anatomical regions and generating a quantitative parameter vector, including the plurality of region-specific quantitative parameters generated for the plurality of respective anatomical regions, as the second quantitative parameter.

The generating may include: extracting at least one second region for the at least one anatomical region based on the quantitative measurement conditions; and generating a second quantitative parameter associated with the at least one second region and the at least one anatomical region by quantifying at least one of the spatial ratio of the space (measured at 2D or 3D) occupied by the at least one second region within the at least one anatomical region and a spatial distribution including the size and number of the at least one second region in association with the at least one anatomical region.

The generating a second quantitative parameter associated with the at least one second region and the at least one anatomical region may include: extracting at least one Low Attenuation Area (LAA) or at least one air trap region (or volume) within the at least one anatomical region as the at least one second region; and generating the spatial ratio of the space (measured at 2D or 3D) occupied by the at least one second region within the at least one anatomical region as the second quantitative parameter associated with the at least one second region and the at least one anatomical region.

The generating a second quantitative parameter associated with the at least one second region and the at least one anatomical region may include: extracting at least one Low Attenuation Area (LAA) within the at least one anatomical region as the at least one second region; and generating the second quantitative parameter associated with the at least one second region and the at least one anatomical region based on a spatial distribution including the number of at least one second region based on (according to) the size of the at least one second region within the at least one anatomical region.

The generating a second quantitative parameter for at least one anatomical region may include: segmenting an airway region within the at least one anatomical region; calculating a lumen perimeter and a wall area using a segmented lumen and airway wall; and generating, for each of at least one airway included in the at least one anatomical region, an airway wall area, normalized on the assumption that the perimeter of the lumen is 10 mm, as the second quantitative parameter.

According to still another aspect of the present invention, there is provided a computing system for performing medical image analysis, the computing system including at least one processor, wherein the at least one processor is configured to: perform image processing on a first medical image, and segment at least one anatomical region in the first medical image; generate a first quantitative parameter for the at least one anatomical region based on quantitative measurement conditions that can be measured in the first medical image; and store the first quantitative parameter in a database in association with the first medical image and the at least one anatomical region.

The at least one processor may be further configured to: segment a plurality of anatomical regions in the first medical image; and generate a plurality of region-specific quantitative parameters for the plurality of respective anatomical regions, and generate a quantitative parameter vector, including the plurality of region-specific quantitative parameters generated for the plurality of respective anatomical regions, as the first quantitative parameter.

According to still another aspect of the present invention, there is provided a computing system for performing similar case retrieval, the computing system including at least one processor, wherein the at least one processor is configured to: receive a second medical image via user input; perform image processing on the second medical image, and segment at least one anatomical region in the second medical image; generate a second quantitative parameter for at least one anatomical region based on quantitative measurement conditions that can be measured in the second medical image; and retrieve at least one first medical image having a first quantitative parameter similar to the second quantitative parameter of the second medical image from a database based on a similarity with the second quantitative parameter.

The at least one processor may be further configured to: segment a plurality of anatomical regions in the second medical image; and generate a plurality of region-specific quantitative parameters for the plurality of respective anatomical regions, and generate a quantitative parameter vector, including the plurality of region-specific quantitative parameters generated for the plurality of respective anatomical regions, as the second quantitative parameter.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE DISCLOSURE

Other objects and features of the present invention in addition to the above objects will be apparent from the following description of embodiments taken in conjunction with the accompanying drawings.

Embodiments of the present invention will be described in detail below with reference to the accompanying drawings. In the following description of the present invention, when it is determined that a detailed description of a related known component or function may unnecessarily make the gist of the present invention obscure, it will be omitted.

Figure 1:
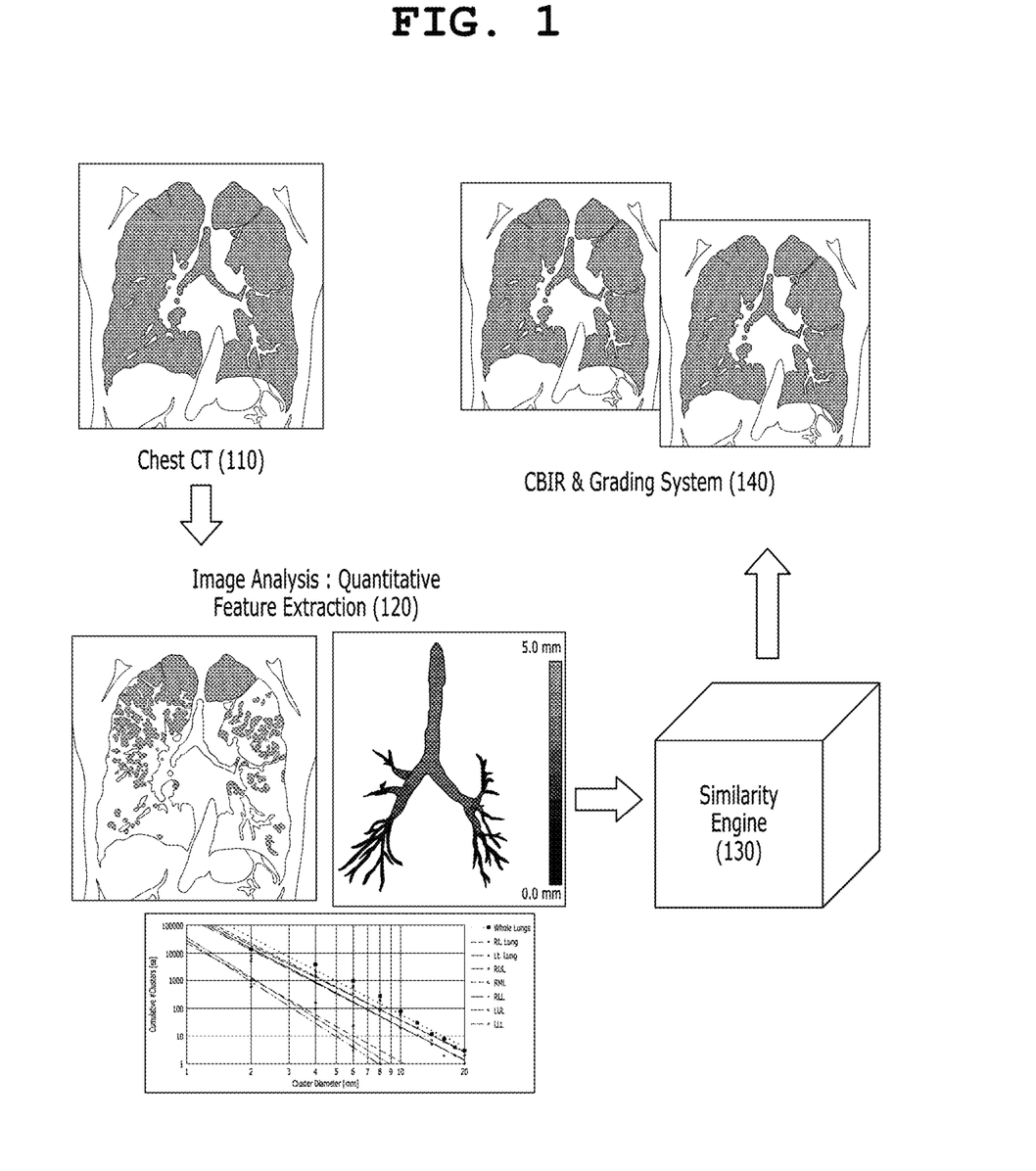
FIG. 1 is a diagram showing an overview of the operation of a medical image analysis system according to an embodiment of the present invention.

FIG. 1 is a diagram showing an overview of the operation of a medical image analysis system according to an embodiment of the present invention. The medical image analysis system shown in FIG. 1 includes a computing system (not shown), and the computing system may include a processor, memory, a database, and/or a communication module. The following operations and functions may be performed by the processor in the computing system, and the processor may perform the following operations and functions in cooperation with at least one of the memory, the database, and the communication module.

Referring to FIG. 1, the medical image analysis system receives or acquires a chest medical image 110. The medical image analysis system performs image analysis 120 on the chest medical image 110, and extracts quantitative features. The medical image analysis system includes a similarity engine 130 configured to determine similarity based on the quantitative features. The similarity engine 130 may convert and represent the quantitative features, acquired for the medical image 110, into and as a quantitative parameter so that similar case retrieval is enabled. The quantitative parameter may include a plurality of types of quantitative features, and the quantitative features may be classified for and allocated to respective anatomical regions. The quantitative features allocated to the plurality of respective anatomical regions may be mapped into a vector space, and thus the quantitative parameter may be represented by a vector of quantitative features. In order to map the quantitative parameter to the plurality of respective anatomical regions, the process of segmenting at least one anatomical region in the medical image 110 through image segmentation needs to precede.

A retrieval and grading system 140 may compare the quantitative parameter of the medical image 110 generated by the similarity engine 130, may allocate rankings according to similarity, and may retrieve one or more existing medical images closest to the given medical image 110. A Content-Based Image Retrieval (CBIR) technique may be employed, and the retrieval and grading system 140 of the present invention performs CBIR based on quantitative parameters.

The quantitative parameters are represented by vectors of quantitative features, and are mapped into the vector space. Accordingly, when rankings are allocated according to the similarity, the similarity may be determined based on the distances in the vector space between the quantitative parameters of medical images.

When a first medical image is received or acquired, the image analysis 120 is performed on the first medical image, and first quantitative features of the first medical image are extracted. The first quantitative features are converted into and generated as a first quantitative parameter by the similarity engine 130. The first quantitative parameter is associated with the first medical image and then stored in a database.

When a second medical image, which is a target for which a user wants to retrieve one or more similar cases, is acquired by the input of the user or is received, the image analysis 120 is performed on the second medical image, and second quantitative features of the second medical image are extracted. The second quantitative features are converted into and generated as a second quantitative parameter by the similarity engine 130.

The retrieval and grading system 140 may retrieve the first quantitative parameter, the distance of which in the vector space is closest to the second quantitative parameter, from the database, and may provide the first medical image, stored in association with the first quantitative parameter, as a similar case to the second medical image. The second medical image may have one or more similar cases, and a plurality of similar cases may be sequentially displayed based on their similarity rankings.

A specific configuration of the present invention will be described by taking the lung region as an example below. The spirit of the present invention should not be understood as being limited by the following embodiments.

Examples of the types of quantitative features are as follows.

A Low Attenuation Area (LAA), LAA size analysis, AWT-Pi10, which is an index indicative of the relative thickness of the airway wall, and the analysis of an air trap, which is the area where air is trapped in the alveoli, may be used for quantitative features.

These quantitative features may be calculated for each of the anatomical regions segmented within the lung area. When the quantitative features are generalized and represented, they may be represented by {Parameter}_{Region}. The anatomical regions may be classified into the whole lungs, the left lung, the right lung, the left upper lobe, the left lower lobe, the right upper lobe, the right middle lobe, and the right lower lobe.

The medical image analysis system of the present invention may retrieve one or more similar cases with spatial distribution taken into account by using quantitative parameters, obtained by matching quantitative features to each anatomical region and then performing analysis, for similarity analysis.

For example, LAA parameters may be acquired and represented for respective anatomical regions, as follows:
LAA_WholeLung, LAA_LeftLung, LAA_RightLung,
LAA_LeftUpperLobe, LAA_LeftLowerLobe,
LAA_RightUpperLobe, LAA_RightMiddleLobe,
LAA_RightLowerLobe The LAA refers to a region in which a brightness value is darker than a threshold value on a CT image. The LAA is known clinically to mean an inactive area within the lung region.

Figure 2:
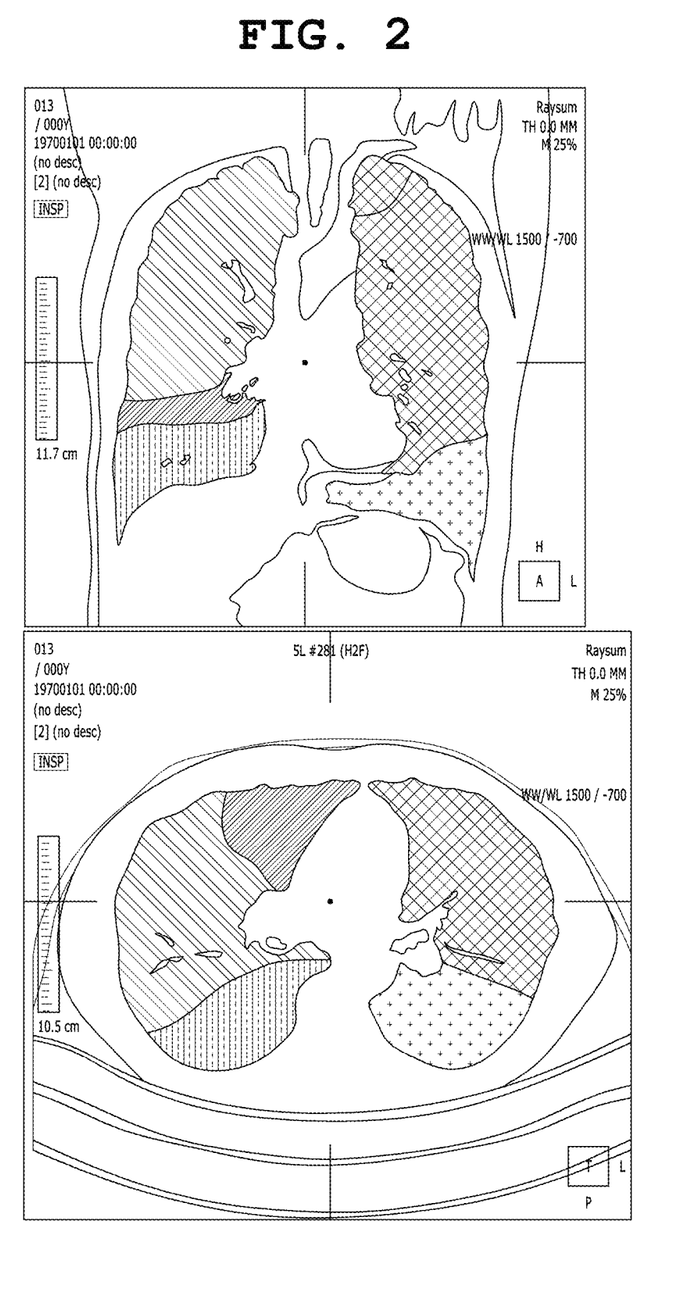
FIG. 2 shows views illustrating an example of lung lobe segmentation in a medical image analysis process according to an embodiment of the present invention.

FIG. 2 shows views illustrating an example of lung lobe segmentation in a medical image analysis process according to an embodiment of the present invention.

In the CT image including the lungs, the overall area of the lungs is segmented from other organs. The left and right regions of the lung are then segmented from each other. From these, whole lungs, left lung, and right lung regions are acquired, and an LAA may be specified for each of the regions.

Referring to FIG. 2, a CT image including the lungs is shown. A coronal image and an axial image are shown by FIG. 2, and the image that is shown in the coronal image is an image in which the left and right sides thereof are reversed. The left lung is segmented into the left upper lobe and the right lower lobe, and the right lung is segmented into the right upper lobe, the right middle lobe, and the right lower lobe.

Quantitative parameters including an LAA may be calculated for each of the whole lungs, the left lung, the right lung, the left upper lobe, the left lower lobe, the right upper lobe, the right middle lobe, and the right lower lobe. These may function as clinically significant quantitative features for the medical image 110, and may be used as reference indices for similar case retrieval. The per-anatomical region spatial distribution of LAAs, the per-anatomical region spatial distribution of airway wall thicknesses, and the per-anatomical region spatial distribution of inactive areas may be sufficient factors to characterize the medical image 110 from a clinical point of view.

Figure 3:
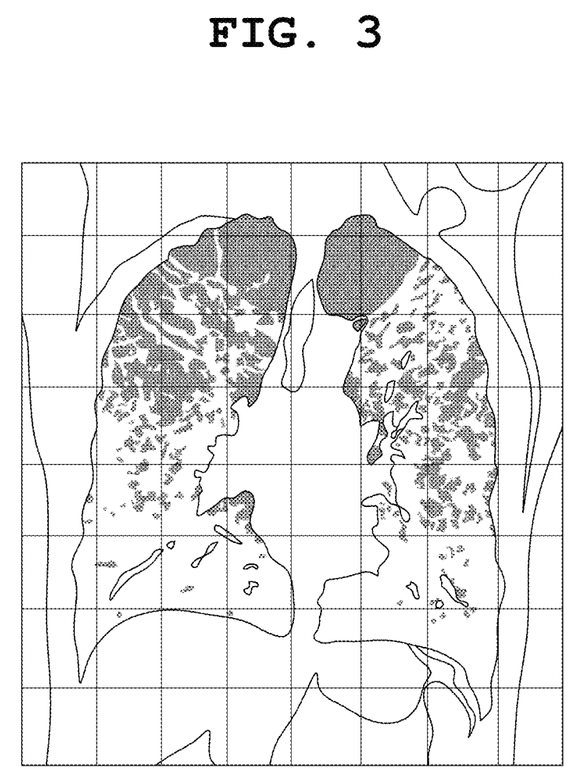
FIG. 3 is a view illustrating an example of low attenuation area (LAA) detection in a medical image analysis process according to an embodiment of the present invention.

FIG. 3 is a view illustrating an example of low attenuation area (LAA) detection in a medical image analysis process according to an embodiment of the present invention.

Referring to FIG. 3, in a CT image including the lungs, a region having a Hounsfield value of −950 HU or less may be classified and displayed as an LAA. In the CT image, a region having a value of −950 HU is classified as an area filled with air due to the rupture of the alveoli. The region classified as the LAA may be understood as a region that does not actually help breathing.

In FIG. 3, regions detected as LAAs are classified and displayed throughout the whole lung area. The LAA detection regions are mapped into the anatomical regions segmented in FIG. 2, and the LAA detection regions may be classified and quantified for each of the whole lungs, the left lung, the right lung, the left upper lobe, the left lower lobe, the right upper lobe, the right middle lobe, and the right lower lobe.

−950 HU, which is a reference brightness value for the detection of an LAA, is an exemplary value, and the present invention is not limited thereto. The value may be changed or adjusted.

Meanwhile, in FIG. 3, the CT image including the lungs is partitioned into equal spaces, which is only intended for helping visual understanding and has no clinical significance.

Figure 4:
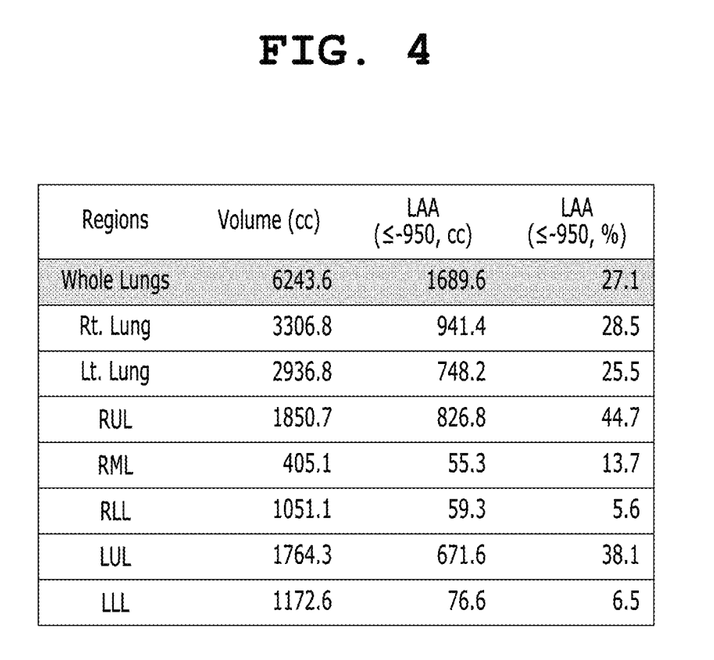
FIG. 4 is a view illustrating an example of the calculation of an LAA ratio for each segmented lung lobe in a medical image analysis process according to an embodiment of the present invention.

FIG. 4 is a view illustrating an example of the calculation of an LAA ratio for each segmented lung lobe in a medical image analysis process according to an embodiment of the present invention.

Referring to FIG. 4, the total volume of each segmented anatomical region is obtained, and the volumes of Low Attenuation Areas (LAAs) detected in each segmented anatomical region are summed and calculated. Accordingly, the ratio of the LAA volume to the total volume may be calculated for each anatomical region. The rightmost column of FIG. 4 lists the % LAA information obtained as described above, and shows values obtained through multiplication by 100 to represent them in percentages.

The rows of FIG. 4 correspond to the whole lungs (Whole Lungs), the right lung (Rt. Lung), the left lung (Lt. Lung), the right upper lung lobe (RUL), the right middle lung lobe (RML), the right lower lung lobe (RLL), the left upper lung lobe (LUL), and the left lower lung lobe (LLL), and each of the columns of FIG. 4 shows the total volume (cc), the LAA volume, and the % LAA for a corresponding anatomical region.

Figure 5:
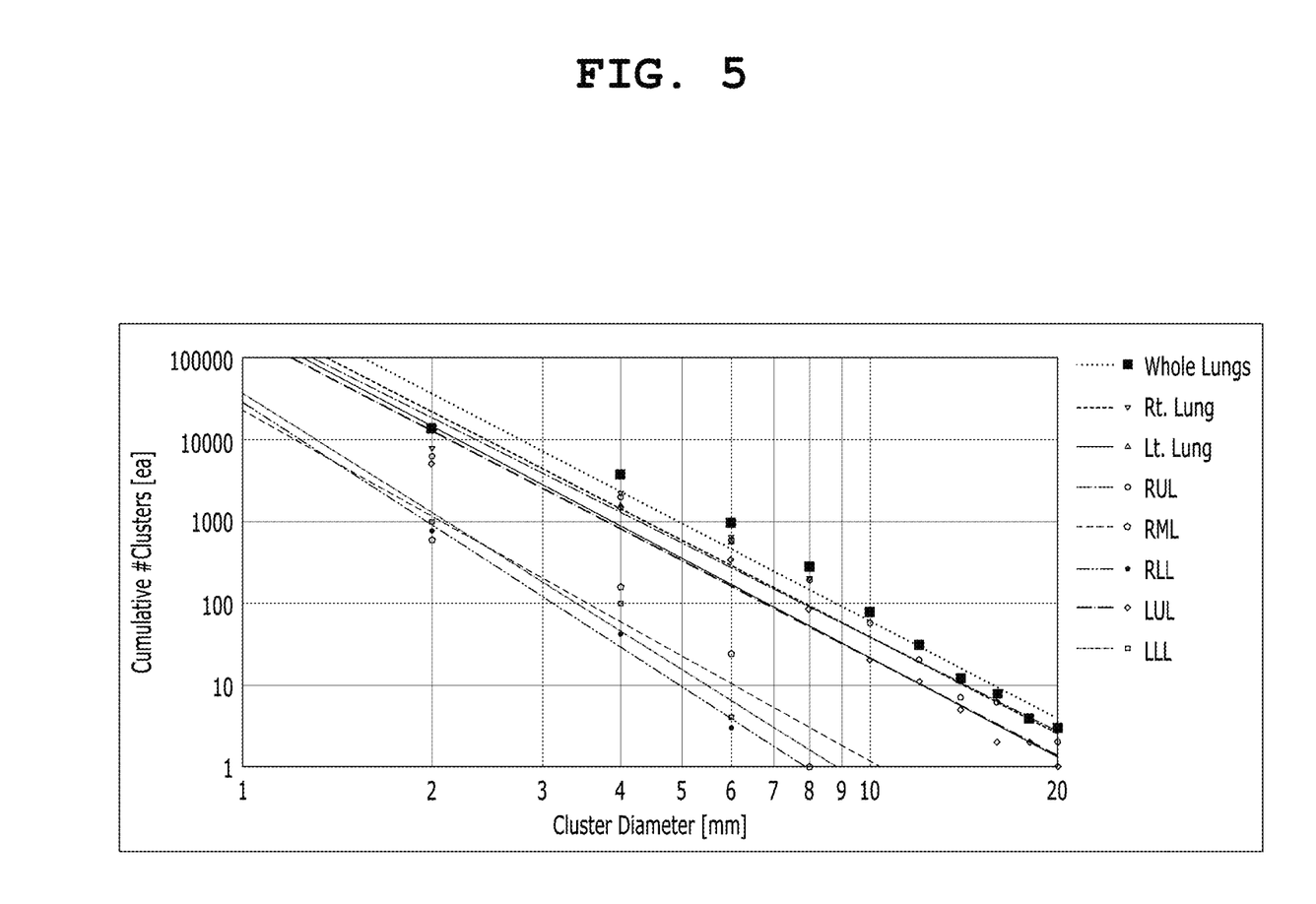
FIG. 5 is a view illustrating an example of the logarithmic analysis of a LAA size for each segmented lung lobe in a medical image analysis process according to an embodiment of the present invention.

FIG. 5 is a view illustrating an example of the logarithmic analysis of a LAA size for each segmented lung lobe in a medical image analysis process according to an embodiment of the present invention. Each of LAA (assumed as first region for this embodiment) can be classified by its size (for example, diameter) and the number of LAA can be determined based on the size.

The LAA size analysis is referred to as LAASA for convenience of description. The LAAs obtained in FIG. 3 are classified by size. For example, the LAAs may be classified as being less than 2 mm, as being 2 mm or more and less than 4 mm, as being 4 mm or more and less than 6 mm, as being 6 mm or more and less than 8 mm, as being 8 mm or more and less than 10 mm, as being 10 mm or more and less than 12 mm, as being 12 mm or more and less than 14 mm, as being 14 mm or more and less than 16 mm, as being 16 mm or more and less than 18 mm, as being 18 mm or more and less than 20 mm, or as being 20 mm or more.

The numbers of classified LAAs are counted. Using these, the horizontal axis represents the size of the LAA and the vertical axis represents the spatial distribution of the LAA in terms of the number of accumulated areas, as shown in FIG. 5.

In FIG. 5, both the horizontal and vertical axes are shown in log scale. The cumulative numbers of the vertical axis of FIG. 5 represent the numbers of LAAs having a size of 0 mm or more, a size of 2 mm or more, a size of 4 mm or more, a size of 6 mm or more, a size of 8 mm or more, a size of 10 mm or more, a size of 12 mm or more, a size of 14 mm or more, a size of 16 mm or more, a size of 18 mm or more, or a size of 20 mm or more.

When the distribution of the values in FIG. 5 is modeled by a linear equation (liner regression), the slope value of the linear equation is represented by LogLogD.

In FIG. 5, LAASA_LogLogD values are calculated for respective segmented anatomical regions and plotted on a graph. % LAA and LAASA may be used in combination as a quantitative parameter. The value of % LAA may change depending on how far a subject breathed (a respiratory level) when a CT image was acquired. It is clinically known that LogLogD has a constant value regardless of the respiratory level.

Figure 6:
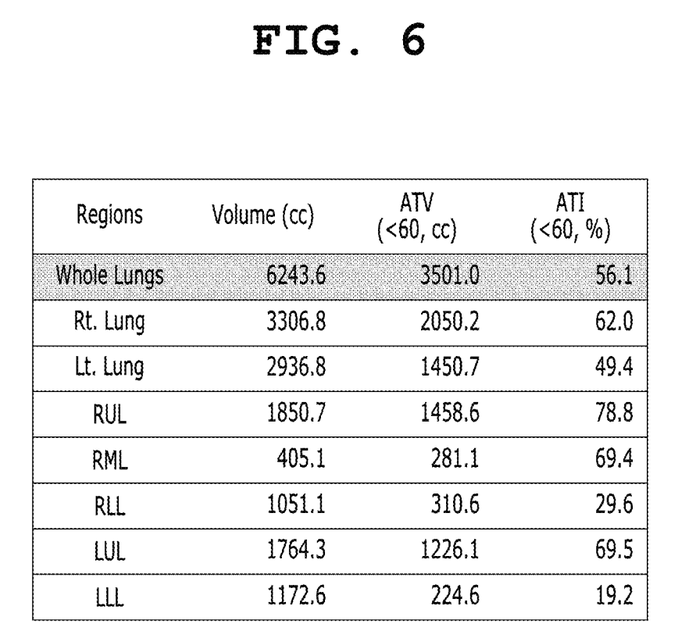
FIG. 6 is a view illustrating an example of the calculation of an air trap ratio for each segmented lung lobe in a medical image analysis process according to an embodiment of the present invention.

FIG. 6 is a view illustrating an example of the calculation of an air trap ratio for each segmented lung lobe in a medical image analysis process according to an embodiment of the present invention.

Referring to FIG. 6, the rows of FIG. 6 correspond to the whole lungs (Whole Lungs), the right lung (Rt. Lung), the left lung (Lt. Lung), the right upper lung lobe (RUL), right middle lung lobe (RML), the right lower lung lobe (RLL), the left upper lung lobe (LUL), and the left lower lung lobe (LLL), and each of the columns of FIG. 4 shows the total volume (cc), the air trap volume (ATV) (cc), and the air trap volume ratio (ATI) (%).

Air trap areas are obtained as follows:

Lung and lobe regions are segmented in an inspiration image.

An expiration image is registered with the inspiration image.

A difference image between the registered expiration image and the inspiration image is generated (the registered expiration image—the inspiration image).

Regions having a value of 60 HU (Hounsfield Unit) or less are detected in the difference image.

The air trap ratio may be calculated by obtaining the ratio between the ATV obtained through the above-described process and the total volume of each anatomical region. In this case, 60 HU is a value that may be changed or adjusted. In a normal case, when a subject expires/exhales, a normal area should be brightened to be more than 60 HU. An area having a value of 60 HU or less refers to an area where air remains in the lung. It also refers to an area where expiration is not performed, and is thus called an air trap region in the sense that air is trapped in the lung.

Figure 7:
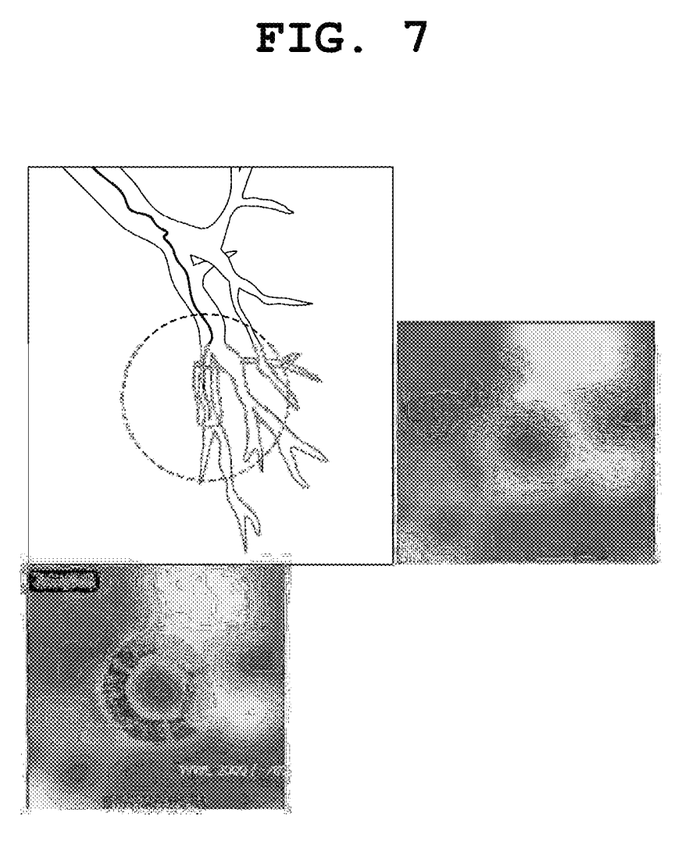
FIG. 7 is a view illustrating an example of obtaining an AWT-Pi10 parameter in a medical image analysis process according to an embodiment of the present invention.

FIG. 7 is a view illustrating an example of obtaining an AWT-Pi10 parameter in a medical image analysis process according to an embodiment of the present invention.

In order to obtain the AWT-Pi10 parameter, lung and lobe regions are segmented in the medical image. Thereafter, the airway is segmented. In each branch of the airway, the lumen and the airway wall are segmented.

In FIG. 7, there is shown the process of selecting a branch of the segmented airway and segmenting the lumen and the airway wall. The airway wall and the lumen are segmented in a CT image, and the results of the segmentation are overlaid and displayed on the CT image. Using the segmented lumen and airway wall, the diameter of the lumen perimeter and the area of the airway wall are calculated. The obtained perimeter and wall area are quantified for the airway included in each of the segmented anatomical areas. In this case, in order to make comparisons based on the same criteria, line regression is performed on the assumption that the perimeter is 10 mm, and the wall area based on the assumption that the perimeter is 10 mm is calculated as AWT-Pi10.

It is known that when the airway wall is thick, there is a high possibility that it is difficult to expire well. In order to represent this quantitatively, the AWT-Pi10 parameter is used. In general, the lumen and airway wall thickness are larger on the trachea side, and the lumen and airway wall thickness are smaller in the direction toward the microbronchi. As the normalization intended to represent the thickness of the airway wall as a single value within a specific anatomical region, the thickness of the airway wall is calculated and used as a quantitative parameter on the assumption that the circumference of the lumen is 10 mm. After values obtained from all airways in the segmented anatomical region have been modeling by a linear equation, the thickness of the airway wall at the time when the perimeter of the lumen is 10 mm is defined as AWT-Pi10 and then used. In this case, the thickness of the airway wall may be defined as using the square root of the area of the airway wall.

In the case of chronic obstructive pulmonary disease (COPD), diffuse lung disease (DLD), and diffuse interstitial lung disease (DILD), the criterion for retrieving clinically significant cases may be expressed as, for example, "it is similar in that the left upper lobe has a lot of LAA and the rest of the area has no LAA." The similarity of a quantitative parameter calculated for each anatomical area plays an important role. In a clinical sense, it is known that the fact that the shape of the lung itself is similar or the fact that the distribution of brightness values is similar does not have considerable significance. Furthermore, according to recent clinical studies, it is common to assign spatial significance to individual lobes rather than assigning spatial significance to the upper and lower, front and rear sides of the lungs. Moreover, the spatial distribution of LAAs within one lobe has no clinical significance because the procedure is performed based on each lobe.

Furthermore, the shape of the lobe varies considerably from patient to patient. In some cases, the number of lobes may be one more than that of normal lobes, or the lobe may not be classified. Accordingly, it is known that dividing the whole lung space into equal spaces and then analyzing them, as shown in FIG. 3, has no considerable clinical significance.

Since the quantitative features mentioned above have different value ranges for respective features, normalization needs to be performed in order to assign normalized or equivalent weight. For each feature, it may be normalized by dividing it by standard deviation or by percentile95.

Normalized parameters may constitute a set. This set may be dealt with as a single vector. For example, a vector collecting quantitative parameters such as {LAA_Whole, LAA_R, LAA_L, LAA_RUL, . . . , AWT-Pi10_RUL, AWT-Pi10_RML, . . . , LogLogD_LUL, LogLogD_LLL} may be obtained as a final quantitative parameter.

The distances between such vectors of quantitative parameters may be calculated using the Euclidean distances or cosine distances in the vector space, and it may be determined that the similarity between the vectors is inversely proportional to the distance therebetween.

Although the similar case retrieval technique supporting the diagnosis of lung disease has been described as an example above, the spirit of the present invention is not limited to the above-described embodiments. The medical image analysis and similar case retrieval system of the present invention extracts quantitative features having clinical significance based on a medical image. The quantitative features may be extracted based on a medical image, and may be mapped to anatomical regions segmented through image segmentation. At least one quantitative feature is obtained for each anatomical region, and one vector may be generated for each medical image or each medical image set by combining one or more quantitative features obtained for individual anatomical regions. In other words, one quantitative parameter vector may be given for one medical image or one medical image set. The quantitative parameter vector contains indices for respective anatomical regions in the medical image. The quantitative parameter vector is a value obtained by normalization between different quantitative features, and is associated with the medical image and then stored in a database.

Thereafter, when a new medical image is input, similarities may be measured based on the distances between a quantitative parameter vector derived through the analysis of the new medical image and existing quantitative parameter vectors stored in the database, and at least one medical image most similar to the new medical image in terms of clinical significance may be retrieved and provided as a similar case.

Figure 8:
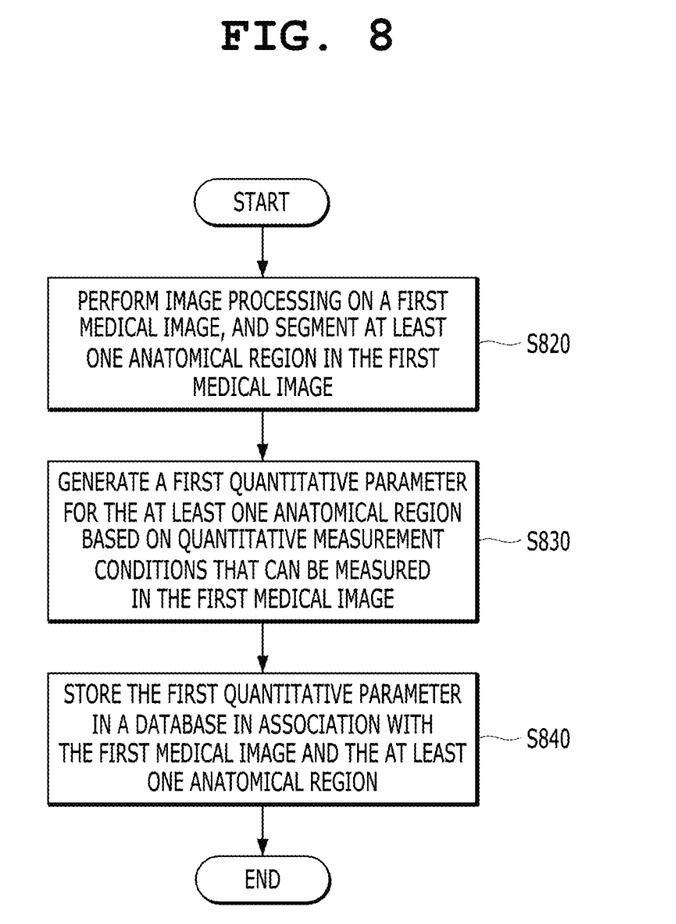
FIG. 8 is an operational flowchart showing a medical image analysis method according to an embodiment of the present invention.

FIG. 8 is a flowchart showing a medical image analysis method according to an embodiment of the present invention.

Referring to FIG. 8, at step S820, a computing system by which a medical image analysis method is performed performs image processing on a first medical image, and segments at least one anatomical region in the first medical image.

At step S830, the computing system generates a first quantitative parameter for the at least one anatomical region based on quantitative measurement conditions that can be measured in the first medical image.

At step S840, the computing system stores the first quantitative parameter in the database in association with the first medical image and the at least one anatomical region.

At step S820, a plurality of anatomical regions may be segmented in the first medical image. In this case, at step S830 of generating the first quantitative parameter, a plurality of region-specific quantitative parameters is generated for a plurality of respective anatomical regions, and a quantitative parameter vector including the plurality of region-specific quantitative parameters generated for the plurality of respective anatomical regions may be generated as a first quantitative parameter.

In this case, the first quantitative parameter may be obtained based on the calculation intended to perform adjustment to assign normalized or equivalent weight by normalizing each of the plurality of region-specific quantization parameters in the quantization parameter vector. The quantitative parameter vector may be a feature vector generated by mapping each of the plurality of region-specific quantitative parameters into a vector space.

Step S830 of generating the first quantitative parameter for the at least one anatomical region may include: the step of extracting at least one first region (e.g., an LAA, or an air trap region) for the at least one anatomical region based on the quantitative measurement conditions; and the step (not shown) of generating a first quantitative parameter associated with the at least one first region and the at least one anatomical region by quantifying at least one of the spatial ratio of the space (measured at 2D or 3D) occupied by the at least one first region within the at least one anatomical region and a spatial distribution including the size and number of the at least one first region in association with the at least one anatomical region.

At step S820 of segmenting the at least one anatomical region in the first medical image, a plurality of anatomical regions may be segmented in the first medical image. At the step of extracting the at least one first region for the at least one anatomical region, at least one first region may be extracted for each of the plurality of anatomical regions.

The step (not shown) of generating the first quantitative parameter associated with the at least one first region and the at least one anatomical region may include: the step of extracting at least one Low Attenuation Area (LAA) or at least one air trap region within the at least one anatomical region as the at least one first region; and the step of generating the spatial ratio (% LAA or % air trap) of the space (can be measured as 2D area or 3D volume) occupied by the at least one first region within the at least one anatomical region as the first quantitative parameter associated with the at least one first region and the at least one anatomical region.

The step (not shown) of generating the first quantitative parameter associated with the at least one first region and the at least one anatomical region may include: the step of extracting at least one Low Attenuation Area (LAA) within the at least one anatomical region as the at least one first region; and the step of generating the first quantitative parameter (e.g., LAASA-LogLogD) associated with the at least one first region and the at least one anatomical region based on a spatial distribution including the number of at least one first region based on the size of the at least one first region within the at least one anatomical region. For example, as shown in FIG. 5, each of first region (LAA) can be classified by its size (for example, diameter) and the number of LAA can be determined based on the size.

Step S830 of generating the first quantitative parameter for the at least one anatomical region may include: the step of segmenting the airway region within the at least one anatomical region; the step of calculating a lumen perimeter and a wall area using the segmented lumen and airway wall; and the step of generating, for each of at least one airway included in the at least one anatomical region, a parameter (e.g. AWT-Pi10), based on the airway wall area normalized on the assumption that the perimeter of the lumen is 10 mm, as the first quantitative parameter.

Figure 9:
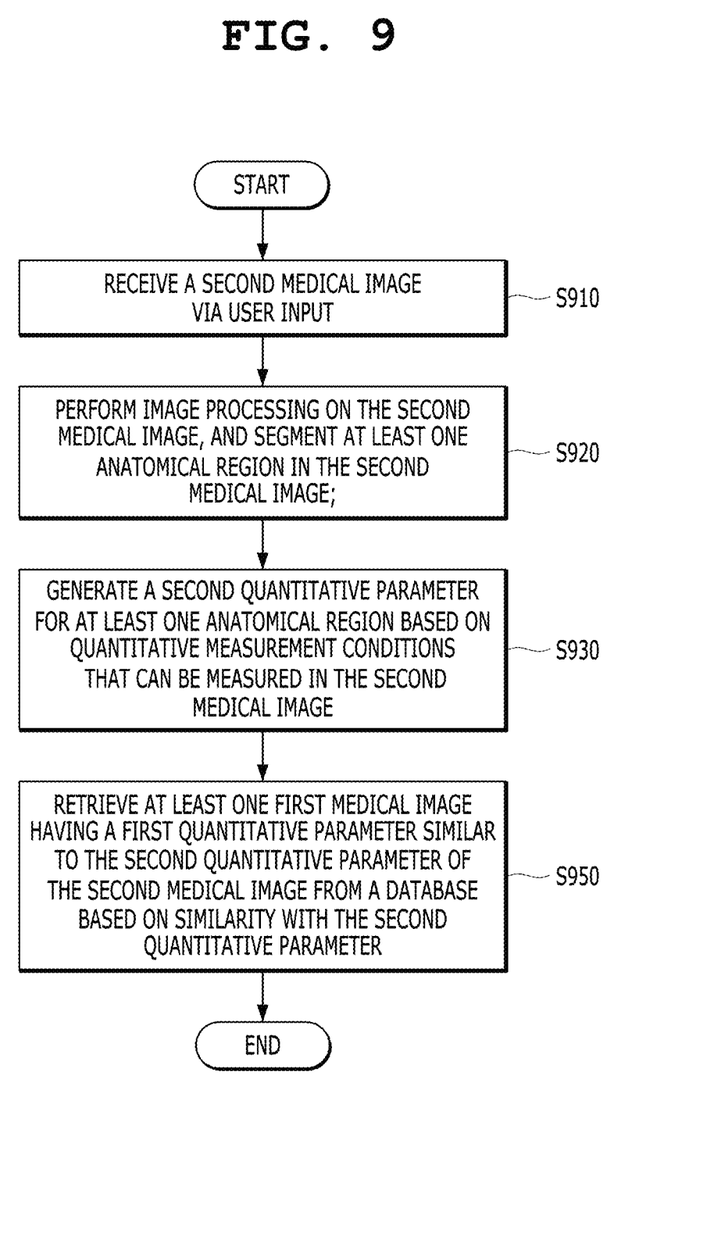
FIG. 9 is an operational flowchart showing a similar case retrieval method according to an embodiment of the present invention.

FIG. 9 is a flowchart showing a similar case retrieval method according to an embodiment of the present invention.

Referring to FIG. 9, a computing system by which the similar case retrieval method is performed receives a second medical image via user input at step S910.

At step S920, the computing system performs image processing on the second medical image, and segments at least one anatomical region in the second medical image.

At step S930, the computing system generates a second quantitative parameter for at least one anatomical region based on quantitative measurement conditions that can be measured in the second medical image.

At step S950, the computing system retrieves at least one first medical image having a first quantitative parameter similar to the second quantitative parameter of the second medical image from the database based on the similarity with the second quantitative parameter.

The computing system may store the second medical image, for which similar case retrieval and review have been completed, in the database in association with the at least one anatomical region and the second quantitative parameter (not shown).

At step S920 of segmenting the at least one anatomical region in the second medical image, a plurality of anatomical regions may be segmented in the second medical image. At step S930 of generating the second quantitative parameter, a plurality of region-specific quantitative parameters may be generated for the plurality of respective anatomical regions, and a quantitative parameter vector including the plurality of region-specific quantitative parameters generated for the plurality of respective anatomical regions may be generated as the second quantitative parameter.

Step S930 of generating the second quantitative parameter for the at least one anatomical region may include: the step of extracting at least one second region (e.g., an LAA, or an air trap region) for the at least one anatomical region based on the quantitative measurement conditions; and the step (not shown) of generating a second quantitative parameter associated with the at least one second region and the at least one anatomical region by quantifying at least one of the spatial ratio of the space (can be measured as 2D area or 3D volume) occupied by the at least one second region within the at least one anatomical region and a spatial distribution including the size and number of the at least one second region in association with the at least one anatomical region.

The step (not shown) of generating the second quantitative parameter associated with the at least one second region and the at least one anatomical region may include: the step of extracting at least one Low Attenuation Area (LAA) or at least one air trap region within the at least one anatomical region as the at least one second region; and the step of generating the spatial ratio (% LAA or % air trap) of the space (can be measured as 2D area or 3D volume) occupied by the at least one second region within the at least one anatomical region as the second quantitative parameter associated with the at least one second region and the at least one anatomical region.

The step (not shown) of generating the second quantitative parameter associated with the at least one second region and the at least one anatomical region may include: the step of extracting at least one Low Attenuation Area (LAA) within the at least one anatomical region as the at least one second region; and the step of generating the second quantitative parameter (e.g., LAASA-LogLogD) associated with the at least one second region and the at least one anatomical region based on a spatial distribution including the number of at least one second region based on (according to) the size of the at least one second region within the at least one anatomical region.

Step S930 of generating the second quantitative parameter for the at least one anatomical region may include: the step of segmenting the airway region within the at least one anatomical region; the step of calculating a lumen perimeter and a wall area using the segmented lumen and airway wall; and the step of generating, for each of at least one airway included in the at least one anatomical region, a parameter (e.g. AWT-Pi10), based on the airway wall area normalized on the assumption that the perimeter of the lumen is 10 mm, as the second quantitative parameter.

The medical image analysis method and/or similar case retrieval method according to an embodiment of the present invention may be implemented in the form of program instructions executable by a variety of computer means, and may be stored in a computer-readable storage medium. The computer-readable storage medium may include program instructions, a data file, and a data structure solely or in combination. The program instructions which are stored in the medium may be designed and constructed particularly for the present invention, or may be well known and available to those skilled in the field of computer software. Examples of the computer-readable storage medium include magnetic media such as a hard disk, a floppy disk and a magnetic tape, optical media such as CD-ROM and a DVD, magneto-optical media such as a floptical disk, and hardware devices particularly configured to store and execute program instructions such as ROM, RAM, and flash memory. Examples of the program instructions include not only machine language code that is constructed by a compiler but also high-level language code that can be executed by a computer using an interpreter or the like. The above-described hardware components may be configured to act as one or more software modules that perform the operation of the present invention, and vice versa.

However, the present invention is not limited and restricted to the embodiments. Throughout the drawings, the same reference symbols denote the same members. The lengths, heights, sizes, widths, etc. introduced in the embodiments and drawings of the present invention may be exaggerated to help an understanding of the present invention.

According to the present invention, there may be implemented the technology for the retrieval of clinically significant similar cases.

According to the present invention, the database may be constructed in order to support similar case retrieval, effective quantitative parameters may be derived in order to construct the database, and the medical image analysis technology using the quantitative parameters may be implemented.

According to the medical image analysis technology of the present invention, similar case retrieval may be effectively supported and more cases and a larger amount of information may be presented upon the retrieval of similar cases.

According to the present invention, quantitative parameters quantified to calculate similarity may be derived in order to retrieve clinically significant similar cases. According to the present invention, each case image may be represented using one quantitative parameter, and similar cases may be retrieved based on the results of evaluation of the similarity between case images.

According to the present invention, parameters effective in the retrieval of similar cases of lung disease may be quantified, similarity may be determined using the quantitative parameters, and similar cases may be retrieved based on the similarity.

While the present invention has been described in conjunction with specific details, such as specific components, and limited embodiments and diagrams above, these are provided merely to help an overall understanding of the present invention. The present invention is not limited to these embodiments, and various modifications and alterations may be made based on the foregoing description by those having ordinary knowledge in the art to which the present invention pertains.

Therefore, the technical spirit of the present invention should not be determined based only on the described embodiments, and not only the following claims but also all equivalents to the claims and equivalent modifications should be construed as falling within the scope of the spirit of the present invention.

What is claimed is:

1. A case retrieval method that is performed by a computing system, the case retrieval method comprising:
   receiving a first medical image via user input;
   obtaining information of at least one anatomical region in the first medical image segmented by image processing for the first medical image;
   obtaining at least one first region providing information for assisting a diagnosis for a specified disease for the at least one anatomical region;
   generating a first quantitative parameter for the at least one anatomical region based on a quantitative measurement condition capable of being measured for the at least one first region in the first medical image; and
   retrieving at least one second medical image having a second quantitative parameter based on the first quantitative parameter of the first medical image from a database,
   wherein the first quantitative parameter and the second quantitative parameter are related to a quantitative measurement of the at least one first region segmented into respective clusters classified into a plurality of groups that are classified by size of the at least one first region, and
   wherein the retrieving the at least one second medical image retrieves the at least one second medical image using the first quantitative parameter and the second quantitative parameter related to the at least one first region extracted as at least one Low Attenuation Area (LAA) or at least one air trap region within the at least one anatomical region.

2. The case retrieval method of claim 1, wherein, the quantitative measurement of the at least one first region segmented into respective clusters classified into the plurality of groups includes a number, a volume, or a volume ratio of the at least one first region.

3. The case retrieval method of claim 1, wherein the retrieving the at least one second medical image retrieves the at least one second medical image using the first quantitative parameter and the second quantitative parameter related to a number of the at least one LAA or the at least one air trap region classified into the plurality of groups by the size of the at least one LAA or the at least one air trap region, a volume or volume ratio of the at least one LAA or the at least one air trap region classified into the plurality of groups by the size of the at least one LAA or the at least one air trap region.

4. A case retrieval method that is performed by a computing system, the case retrieval method comprising:
   receiving a first medical image via user input;
   obtaining information of at least one anatomical region in the first medical image segmented by image processing for the first medical image;
   obtaining at least one first region providing information for assisting a diagnosis for a specified disease for the at least one anatomical region;
   generating a first quantitative parameter for the at least one anatomical region based on a quantitative measurement condition capable of being measured for the at least one first region in the first medical image; and
   retrieving at least one second medical image having a second quantitative parameter based on the first quantitative parameter of the first medical image from a database,
   wherein the first quantitative parameter and the second quantitative parameter are related to at least one of a normalized wall thickness of the at least one first region when the at least one first region has a tubular structure having a wall and a lumen and the lumen is assumed to have a reference diameter, or wall thickness values of the at least one first region relative to a direction toward microstructure of a hierarchical branch of a tubular structure.

5. A computing system for performing case retrieval, the computing system comprising at least one processor, wherein the at least one processor is configured to:
   receive a first medical image via user input;
   obtain information of at least one anatomical region in the first medical image segmented by image processing for the first medical image;
   obtain at least one first region providing information for assisting a diagnosis for a specified disease for the at least one anatomical region;
   generate a first quantitative parameter for the at least one anatomical region based on a quantitative measurement condition capable of being measured for the at least one first region in the first medical image; and
   retrieve at least one second medical image having a second quantitative parameter based on the first quantitative parameter of the first medical image from a database,
   wherein the first quantitative parameter and the second quantitative parameter are related to a quantitative measurement of the at least one first region segmented into respective clusters classified into a plurality of groups that are classified by size of the at least one first region, and wherein the first quantitative parameter and the second quantitative parameter are related to the at least one first region extracted as at least one Low Attenuation Area (LAA) or at least one air trap region within the at least one anatomical region.

6. The computing system of claim 5, wherein the at least one processor is further configured to retrieve the at least one second medical image using the first quantitative parameter and the second quantitative parameter, wherein the quantitative measurement of the at least one first region segmented into respective clusters classified into the plurality of groups includes a number, a volume, or a volume ratio of the at least one first region.

* * * * *